US006440923B1

(12) United States Patent
Lyle et al.

(10) Patent No.: US 6,440,923 B1
(45) Date of Patent: *Aug. 27, 2002

(54) DETERGENT COMPOSITION

(75) Inventors: Ian Gardner Lyle, Hamburg; Tom Matthew Salmon, Buxtehude; Margrit Schopper-Martens, Buxtehude; Elisabeth Winterot, Buxtehude, all of (DE)

(73) Assignee: Unilever Home & Personal Care USA, division of Conopco, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/466,448

(22) Filed: Dec. 17, 1999

(30) Foreign Application Priority Data

Dec. 24, 1998 (GB) ................................. 9828719

(51) Int. Cl.⁷ ........................... C11D 17/00; C11D 1/86; C11D 3/18
(52) U.S. Cl. ................. 510/406; 510/120; 510/123; 510/125; 510/127; 510/131; 510/135; 510/140; 510/158; 510/403; 510/426; 510/439; 424/70.24; 424/70.19; 424/70.21
(58) Field of Search ................. 510/120, 123, 510/125, 127, 131, 135, 140, 158, 406, 426, 439, 403; 424/70.24, 70.19, 70.21

(56) References Cited

U.S. PATENT DOCUMENTS

| 3,541,581 | A |   | 11/1970 | Monson ...................... 424/70 |
| 4,772,427 | A |   | 9/1988 | Dawson et al. ............. 252/559 |
| 5,334,325 | A | * | 8/1994 | Chaussee ............... 252/174.16 |

FOREIGN PATENT DOCUMENTS

| DE | 38 39 349 | 6/1989 |
| EP | 0247766 | 12/1987 |
| EP | 0259843 | 3/1988 |
| EP | 0753558 | 1/1997 |
| EP | 0820755 | 1/1998 |
| GB | 2172298 | 9/1986 |
| GB | 2179052 | 2/1987 |
| GB | 2213160 | 8/1989 |
| JP | 9-0077629 | 3/1997 |
| WO | 88/05812 | 8/1988 |
| WO | 96/09032 | 3/1996 |
| WO | 97/03646 | 2/1997 |
| WO | 97/16168 | 5/1997 |

* cited by examiner

*Primary Examiner*—Mark Kopec
*Assistant Examiner*—Brian P. Mruk
(74) *Attorney, Agent, or Firm*—Ronald A. Koatz

(57) ABSTRACT

A packaged aqueous self foaming liquid cleansing composition comprising a base composition comprising a surfactant system comprising an anionic surfactant and an amphoteric or zwitterionic surfactant and a hydrophobic component, and a post foaming agent, wherein the composition is substantially free of soap and thickens on the addition of the post foaming agent to the base composition.

21 Claims, No Drawings

DETERGENT COMPOSITION

The present invention relates to detergent compositions suitable for topical application for cleansing the human body, such as the skin and hair. In particular, it relates to self foaming gel compositions, conveniently propellant driven and of the "bag-in-can" variety, which are suitable for use as cleansing compositions, and in particular for use as shower gels, which are formulated to give mild cleansing and optionally conditioning of the skin, and which are dispensed as a gel but generate a foam which is rich and feels luxurious to use.

Self foaming gel compositions formulated to cleanse the skin are well known. Such products may be considered superior to mousse type cleaning products, which suffer from the disadvantage that when applying a pre-formed mousse onto the skin, the mousse tends to break down and dissipate quickly, without providing substantive lather. In contrast, self-foaming compositions are dispensed initially as viscous liquids or gels, which generate copious amounts of lather as they are spread over the skin and optionally rubbed.

It is also known to formulate products which provide in particular a cleansing benefit, which are in the form of a bag in can gel composition. For example, WO 97/03646 discloses a bag in can cleansing composition which contains a base composition which has a viscosity of at least 9,500 cps, which in practice is achieved by the use of a specified thickener. The composition is said to have superior properties by virtue of the relatively high viscosity, in terms of improved stability and the ability to incorporate higher levels of volatile self foaming agent.

A variety of problems have been found to be associated with such bag in can gel compositions. A particular problem relates to the manufacture of such compositions, and especially how to dose into a bag in can arrangement a gel composition which is not so viscous so as to cause problems in the dosing of that composition, and/or to require the use of specialist equipment to dose the composition. In particular, it is clear from the teaching of WO97/03646 that the composition is required to have a minimum viscosity of 9,500 cps. As such, the composition is difficult to process and dose on conventional filling lines.

An associated problem is that in preparing surfactant based gel compositions which subsequently have a self foaming volatile component (such as a liquifiable propellant gas) dosed into them, a number of these compositions experience a drop in viscosity when the self foaming volatile component is dosed into them. This can be disadvantageous, since it is desirable that the product as dispensed has a good, relatively viscous gel structure. This in turn is so that the dispensed product will not only have good manipulation properties for the user, but also so that the relatively rigid gel structure is able to accommodate a relatively high amount of self foaming agent (e.g. liquifiable propellant gas), and to entrap it relatively well. This is so that the resulting product foams well when lathered (by virtue of the relatively high content of volatile component), but also so that it does not foam prematurely after being dispensed.

It is thought that because of the phenomena described of thinning when the propellant gas is dosed that it is necessary for the base composition to have a relatively high initial viscosity, such that any thinning of the product when propellant gas is dosed which does occur is not too deleterious to the properties of the final product as dispensed.

GB-A-2,213,160 describes a soap free post foaming gel composition comprising a major amount of water, 3–23% of a water soluble anionic alkali metal alkyl ether sulphate surfactant, 1–24% of dispersible nonionic ethoxylated fatty alcohol or fatty ester, and 5–20% saturated aliphatic hydrocarbon foaming agent, with the anionic surfactant and the ethoxylated fatty alcohol or ester being present in predetermined ratios. Compositions according to this teaching are based on the specific combination of the anionic and nonionic surfactants, i.e. the alkyl ether sulphate and the nonionic ethoxylated fatty alcohol or fatty ester, and the criticality of each ingredient in the composition is clearly referred to.

A further problem which may be encountered relates to the stability of such cleansing compositions, especially those compositions which are based on non-soap surfactants. Regarding scap-based compositions, post foaming shaving gels employing soap based formulations are well known in the art. However, fundamentally it is desirable to create a cleansing composition based on non-soap surfactants, since by eliminating or reducing any soap to a low level the mildness of the composition may be improved. However, the inclusion of only a low level of soap means that it can be relatively difficult to structure and stabilise the cleansing composition.

We have found a way of formulating such self foaming gel or viscous liquid compositions such that they can deliver effective cleansing and optionally conditioning of the skin, are relatively easy to manufacture, and also have the desired stability and structure characteristics.

Thus, according to a first aspect of the invention, there is provided a packaged aqueous self foaming liquid cleansing composition comprising a base composition comprising a surfactant selected from anionic, nonionic, amphoteric, zwitterionic or cationic surfactants, and mixtures thereof, a hydrophobic component, and a post foaming agent, wherein the composition is substantially free of soap and thickens on the addition of the post foaming agent to the base composition.

Compositions according to the invention may conveniently be packaged in a so-called bag in can package, in which the cleansing composition is packaged inside a flexible bag, which is itself disposed in a can, with a suitable propellant gas located between the can and bag which pressurises the composition in the bag to a degree where it can be dispersed from suitable hardware.

Alternatively, the composition can be packaged in a pressurised bladder type package, in which the composition is packaged in what amounts to an elasticated bladder, which bladder maintains the contents of the bladder under positive pressure. This pressure is sufficient to cause the contents of the bladder to be dispensed via a closure mechanism located in the package.

In a highly preferred embodiment of the invention, the aqueous composition, shortly prior to being mixed with the self foaming agent, and subsequently being dosed into the product package, has a viscosity of less than 9,000 mPa.s, preferably less than 8,000 mPa.s, more preferably less than 5,000 mPa.s, and even more preferably less than 3,000 mPa.s. It is also highly preferred that packaged composition is prepared by preparing the aqueous base portion of the composition as a somewhat viscous liquid, but excluding the post foaming agent. Just prior (say within 1 minute, preferably with in 10 seconds, preferably within 1 second) to dosing the aqeuous composition into the package of the arrangement (which in the case of a bag in can package is conveniently already located within the can), the post foaming agent is dosed into the aqueous composition, which is then rapidly dosed into a suitable container, such as e.g. a bag within the dispensing package.

However, compositions according to the invention typically thicken on the addition of self foaming agent to form a viscous gel, such that the dispensed composition has good handling and sensory properties, and also such that it retains the post foaming agent well after being dispensed.

By manufacturing the composition in this manner, it is possible to make the aqueous base such that it has a relatively low viscosity, and is therefore easy to process. However, introduction of the post foaming agent into the composition just prior to dosing the composition into the container ensures that any thickening of the composition, which is desirable bearing in mind that the form of the dispensed composition is as a viscous liquid or gel, does not occur until the composition is inside the container. This method therefore simplifies the manufacturing process. Gel compositions according to the invention are not simple propellant driven compositions, and may not be dispensed from conventional propellant driven aerosol packaging, since they are too viscous to dispense from such conventional single compartment propellant driven aerosal packaging. It is also important that the packaged composition does not have any headspace, since if this were to occur it could cause the composition to be dispensed as a mousse.

Where the packaged composition utilises bag in can packaging, compositions according to the invention have two associated gases; a propellant gas and a post (self) foaming agent. The propellant gas is that which is contained within the can, but acts against the outside of the bag in which the composition is contained to dispense the composition when an actuator on the can is used. The propellant gas can be any suitable gas, but is conveniently a non-liquifiable propellant gas, such as compressed air, though any propellant which would function to dispense the composition would be suitable. The propellant gas is present in the packaged composition at any required and suitable level, but is typically present in the packaged product at levels sufficient to produce a satisfactory dispensing pressure, which will typically be 2–12 bar, more preferably 3–9 bar.

The other component required in such packaged composition according to the invention is a post foaming agent. The post foaming agent is present in compositions according to the invention to allow the composition, which is dispensed in the form of a stable gel, once dispensed to generate a foam, as it evaporates on contact with a skin surface, thereby experiencing body heat. The generation of a foam provides a product which has various desirable consumer attributes, including ease of handling and spreading, and desirable sensory properties.

Suitable post foaming agents for inclusion in compositions according to the invention are volatile or liquifiable, and include (but are not limited to) hydrocarbons, such as isobutane and isopentane. Post foaming agents are present in packaged compositions according to the invention at levels of 4–15%, more preferably 5–10% by weight of the packaged composition. Suitable post foaming agents should be capable of being contained in compositions according to the invention as liquids, which may have been formed under the pressure to which the packaged composition has been subjected. As such, it is also desirable and may even be essential that packages in which the packaged composition is stored have no head space, to prevent the premature evaporation of the post foaming agent.

Packaged compositions according to the invention contain a blend of hydrophobic components, including perfume oils and hydrophobic benefit agent components, and hydrocarbon post foaming agents, which are blended and matched, and chosen in conjunction with a suitable surfactant or blend of surfactants, in order to form a stable isotropic system. Compositions according to the invention are often microemulsions.

The hydrophobic component in the composition may conveniently be a benefit agent, a perfume oil, or another hydrophobic component. The composition according to the invention may conveniently be suitable for cleansing, and in addition optionally moisturising, conditioning or protecting the skin. Where the hydrophobic component in the composition is a benefit agent, this may be included in the composition to moisturise, condition and/or protect the skin. By "benefit agent" is meant a substance that softens the skin (stratum corneum) and keeps it soft by retarding the decrease of its water content, and/or protects the skin. However, substantial deposition on the skin of a hydrophobic component or benefit agent is not necessarily a feature of compositions according to the invention.

Preferred hydrophobic components which may be solid or liquid at room temperature, but in compositions according to the invention are to be found in liquid form (either by virtue of being liquid at room temperature themselves, or by being solubilised in a hydrophobic liquid component so as to provide a liquid composition) include:

a) silicone oils, gums and modifications thereof such as linear and cyclic polydimethylsiloxanes, amino, alkyl alkylaryl and aryl silicone oils;

b) fats and oils including natural fats and oils such as jojoba, soyabean, rice bran, avocado, almod, olive, sesame, persic, castor, coconut, milk oils; cacaco fat, beef tallow, lard; hardened oils obtained by hydrogenating the aforementioned oils; and synthetic mono, di and triglycerides such as myristic acid glyceride and 2-ethylhexanoic acid glyceride;

c) waxes such as carnauba, spermaceti, beeswax, lanolin and derivatives thereof;

d) hydrophobic plant extracts;

e) hydrocarbons such as liquid paraffins, petroleum jelly, microcrystalline wax, ceresin, squalene, squalane, and mineral oil;

f) higher fatty acids such as lauric, myristic, palmitic, stearic, behenic, oleic, linoleic linolenic, lanolic, isostearic and poly unsaturated fatty acids (PUFA) acids;

g) higher alcohols such as lauryl, cetyl, steryl, oleyl, behenyl, and 2-hexadecanol alcohol;

h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate for example lauryl lactate, alkyl citrate and alkyl tartrate;

i) essential oils such as fish oils, mentha, jasmine, camphor, white cedar, bitter orange peel, ryu, turpentine, cinnamon, bergamont, citurs unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils;

j) lipids such as cholesterol, ceramides, sucrose esters and pseudo-ceramides as described in European Patent Specification No. 556 957;

k) vitamins such as vitamin A and E, and vitamin alkyl esters, including vitamin C alkyl esters;

l) sunscreens such as octyl methoxyl cinnamate (Parsol MCX) and butyl methoxy benzoylmethane (Parson 1789)

m) phospholipids;

n) perfume oils; and o) mixtures of any of the foregoing components.

Particularly preferred hydrophobic benefit agents include esters such as isopropyl palmitate and myristate, and perfume oils.

The hydrophobic benefit agent is preferably present in an amount of from 0.1 to 20 wt %, more preferably 0.5 to 10%, even more preferably 0.5 to 5 wt % by weight of the composition.

The surfactant or surfactants can be selected from any known surfactant suitable for topical application to the human body, provided that they are blended in such a way as to form a stable isotropic system with the hydrophobic components of the composition. Mild surfactants, i.e. surfactants which do not damage the stratum corneum, the outer layer of skin, are particularly preferred. Because of their lathering properties, anionic surfactants are highly preferred components of compositions according to the invention. Where the composition contains an anionic surfactant, it is preferable that the composition also contains a co-surfactant, which can be a nonionic, cationic amphoteric or zwitterionic surfactant. However, compositions according to the invention are substantially soap free; that is, they contain less than about 1% by weight of soap.

A preferred anionic surfactant is alkyl ether sulphate of formula:

RO(CH$_2$CH$_2$O)$_n$SO$_3$M where R is an alkyl group of 8 to 22 carbon atoms, n ranges from 0.5 to 10 especially from 1.5 to 8, and M is a solubilising cation.

Another preferred anionic surfactant is fatty acyl isethionate of formula:

RCO$_2$CH$_2$CH$_2$SO$_3$M where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Other possible anionic surfactants included alkyl glyceryl ether sulphates, alkyl sulphosuccinates, acyl taurates, acyl sarcosinates, alkyl sulphoacetates, alkyl phosphates, alkyl phosphate esters, acyl lactylates, acyl glutamates and mixtures thereof.

Sulphosuccinates may be monoalkyl sulphosuccinates having the formula:

R$^5$O$_2$CCH$_2$CH(SO$_3$M)CO$_2$M;

and amido-MEA sulphosuccinates of the formula:

R$^5$CONHCH$_2$CH$_2$O$_2$CCH$_2$CH(SO$_3$M)CO$_2$M; wherein R$^6$ ranges from C$_8$–C$_{20}$ alkyl, preferably C$_{12}$–C$_{15}$ alkyl and M is a solubilising cation.

Sarcosinates are generally indicated by the formula: R$^6$CON(CH$_3$)CH$_2$CO$_2$M; wherein R$^5$ ranges from C$_8$–C$_{20}$ alkyl, preferably C$_{12}$–C$_{16}$ alkyl and M is a solubilising cation.

Taurates are generally identified by the formula: R$^5$CONR$^6$CH$_2$CH$_2$SO$_3$M; wherein R$^5$ ranges from C$_2$–C$_{20}$ alkyl, preferably C$_{12}$–C$_{15}$ alkyl, R$^6$ ranges from C$_1$–C$_4$ alkyl, and M is a solubilising cation.

Harsh surfactants such as primary alkane sulphonate or alkyl benzene sulphonate will generally be avoided.

If the surfactant comprises soap, the soap is preferably derived from materials with a C$_5$ to C$_{22}$ substantially saturated carbon chain and, preferably, is a potassium soap with a C$_{12}$ to C$_{16}$ carbon chain.

Suitable nonionic surfactants include alkyl polysaccharides, lactobionamides, ethyleneglycol esters, glycerol monoethers, polyhydroxyamides (glucamide), primary and secondary alcohol ethoxylates, especially the C$_8$–C$_{20}$ aliphatic alcohols ethoxylated with an average of from 1 to 20 moles of ethylene oxide per mole of alcohol. Other suitable nonionics include oil in water emulsifiers such as PEG-40 hydrogenated castor oil.

Suitable further surfactant materials are zwitterionic detergents which have an alkyl or alkenyl group of 7 to 18 carbon atoms and comply with an overall structural formula:

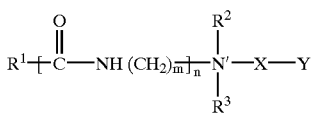

where R$^1$ is alkyl or alkenyl of 7 to 18 carbon atoms R$^2$ and R$^3$ are each independently alkyl, hydroxyalkyl or carboxyalkyl of 1 to 3 carbon atoms;

m is 2 to 4;

n is 0 to 1;

x is alkylene of 1 to 3 carbon atoms optionally substituted with hydroxyl; and

Y is —CO$_2$ or —SO$_3$.

Zwitterionic surfactants within the above general formula include simple betaines of formula:

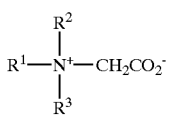

and amido betaines of formula;

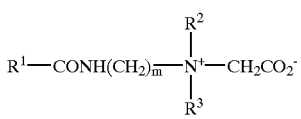

where m is 2 or 3.

In both formulae R$^1$, R$_2$ and R$_3$ are as defined previously.

R$^1$ may, in particular, be a mixture of C$_{12}$ and C$_{14}$ alkyl groups derived from coconut so that at least half, preferably at least three quarters, of the group R$^1$ has 10 to 14 carbon atoms. R$^2$ and R$^3$ are preferably methyl.

A further possibility is a sulphobetaine of formula:

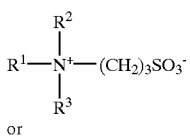

or

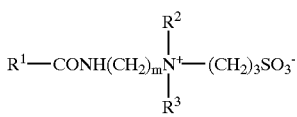

where m is 2 or 3, or variants of these in which —(CH$_2$)$_3$SO$_3$$^-$ is replaced by

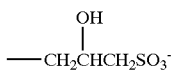

$R^1$, $R^2$ and $R^3$ in these formulae are as defined previously.

Mixtures of any of the foregoing surfactants may also be used.

The surfactants is preferably present at a level of from 10 to 35 wt %, preferably 12 to 30 wt % of the composition.

An optional component in compositions according to the invention is a cationic polymer, such as for example cationic celluloses.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their JAGUAR trademark series).

Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic polymer is selected from cationic cellulose and cationic guar derivatives. Particularly preferred cationic polymers are JAGUAR C13S, JAGUAR C15, JAGUAR C17 and JAGUAR C16 and JAGUAR C162, especially Jaguar C13S.

Cationic polymer if present in compositions according to the invention is present at levels of 0.01–1.2%, more preferably 0.05–1.0%, even more preferably 0.1–0.5% by weight of the composition.

In some embodiments an auxiliary structurant or thickener may be added to the composition. Suitable structurant material include swelling clays, for example laponite; cross-linked polyacrylates such as Carbopol (TM) (polymers available from Goodrich); actylates and copolymers thereof; polyvinylpyrrolidone and copolymers thereof; polyethylene imines; polymeric carboxylates, consisting of and including modified and unmodified starches, unsubstituted guar gums, agars, alginates, xanthan gum, carrageenan, cellulose derivatives, exudate gum, gellan gum, gelatin, pectins and seed gums; gellants; and mixtures thereof.

Preferred thickeners for the composition include fumed silica; alkyl silicone waxes; aluminum silicate; fatty acids and derivatives thereof, in particular, fatty acid monoglyceride polyglycol ethers; polyammonium stearate; hydrotalcites; and mixtures thereof. A particularly preferred thickener is PEG-120 methyl glucose dioleate.

The composition may also comprise a viscosity modifying agent, ie a material which adjusts the viscosity of the composition to be that which is suitable for and preferred by consumers. Suitable materials include ethylene glycols, propylene glycols, salts such as sodium chloride and ammonium sulphate; and sucrose esters.

Further examples of structurants and thickeners are given in the International Cosmetic Ingredient Dictionary, Seventh Edition, 1997, published by CTFA (The Cosmetic, Toiletry & Fragrance Association), incorporated herein by reference.

Compositions of the invention may be formulated as propellant driven and dispensed products for washing the skin, for example, bath or shower gels, hand washing compositions or facial washing liquids, and products for washing the hair, as well as post foaming shaving gels. Shower gels, and also post foaming shaving gels are particularly preferred product forms.

Other typical optional components of such compositions include opacifiers, preferably at 0.2 to 2.0 wt %; preservatives, preferably at 0.2 to 2.0 wt %; pH adjusters, typically at 0.05–2.0 wt %; colourants, preferably at 0.05–2.0 wt %; biological extracts, preferably at 0.05–2.0 wt %; humectants, such as glycerol or sorbitol, preferably at 0.1–10.0 wt %; and perfumes, preferably at 0.5 to 2.0 wt %.

The invention will be further illustrated by reference to the following non-limiting examples.

EXAMPLES

Examples 1–3 represent the aqueous phases of compositions according to the invention for packaging in a bag in can type of package.

| INCI Name | wt (%) | | |
|---|---|---|---|
| | 1 | 2 | 3 |
| Sodium laureth sulphate, 2EO | 10.0 | 12.5 | 10.0 |
| Cocoamidopropyl betaine | 4.0 | 5.0 | 40 |
| Guar hydroxypropyltrimonium chloride | 0.15 | 0.15 | 0.15 |
| Citric acid | 0.325 | 0.238 | 0.24 |
| Sodium benzoate | 0.5 | 0.5 | 0.5 |
| Peach extract + Propylene glycol + Water | 0.2 | 0.2 | 0.2 |
| PEG-120 methyl glucose dioleate | 1.75 | 1.68 | 1.68 |
| Isopropyl palmitate | 0.5 | 1.0 | 1.0 |
| Sodium hydroxide | 0.012 | — | — |
| CI 47005 (dye) | 0.0102 | 0.0102 | 0.0102 |
| CI 45100 (dye) | 0.00072 | 0.00072 | 0.0007 |
| Perfume | 1.0 | 1.0 | 1.0 |
| PEG-40 Hydrog. castor oil | — | 0.5 | 0.5 |
| Water | | to 100 | |
| pH | 4.96 | 5.02 | 4.92 |
| Viscosity (mPA s) | 4300 | 1100 | 80 |

Compositions 1–3 may be made according to the method described below.

In a suitable preparation method, for which the exact amounts of each component can be adjusted according to the amounts actually present in the final composition, 809 g of water is heated to 50° C. and 10 g of sodium benzoate is first dissolved in this. To this is added 290 g of sodium laureth sulphate 2EO and a further 522 g of water, with stirring. 266 g of cocamidopropyl betaine is then added and stirring continued to dissolve the surfactants. 10 g of isopropyl palmitate and 4 g of peach extract are next mixed in. The colourants, dissolved in 10 g water at 20° C., are then added. 3 g of guar hydroxypropyltrimonium chloride and 36 g of PEG-120 methyl glucose dioleate is dissolved in 20 g of perfume oil, and added to the cooled mixture, with stirring. Finally the product pH is adjusted to 4.9 with citric acid (ca. 6.5 g) and sufficient water is added to bring the total sample weight to 2 kg (ca 13.5 g).

The base product is allowed to equilibrate for at least 24 hours before falling into aerosal cans, where 92 wt % of the base composition is combined with 8 wt % of the volatile hydrocarbon self foaming agent. Aluminium cans are pressurised with compressed air at 2.5 bar and sealed by insertion of the valve/diptube/laminated bag assembly before adding the aqueous base, which is mixed with the volatile foaming agent (a mixture comprising 75% isopentane and 25% isobutane) and filled into the bag through the valve in a single operation by use of a specialised machine, such as the "Undercup" Crimper P 2002-500, available from Pamasol, Switzerland.

EXAMPLES 4–9

Compositions 4–9 were prepared according to the preparation method described in conjunction with Examples 1–3 above, and were subjected to evaluation tests regarding their separation on addition of self foaming agent, turbidity and consistency.

The compositions were evaluated as described below.

Laboratory Evaluation Methods

Viscosities of the base formulations were measured at 30° C. using a Haake VT-500 Viscotester, MV 2 Spindle Nos 3, 4, 5 depending on viscosity range. Shear rate was $1s^{-1}$.

The effects of mixing the various aqueous formulations 4–9 with volatile foaming agents were evaluated by a simple laboratory test in which n-pentane was used as a model hydrocarbon liquid. 40 g of the aqueous base was first weighed into a heavy glass screw-top bottle. To this was added 2.1 g or 4.4 g of n-pentane (to achieve 5% or 10% volatile content by weight) and the bottle was immediately closed tightly and shaken vigorously for 1 minute. The sample was then left to stand overnight at room temperature, and was examined the following day. Separation, turbidity and consistency were evaluated on a 3-point scale

|  | 4 | 5 | 6 | 7 | 8 | 9 |
| --- | --- | --- | --- | --- | --- | --- |
| SLES 2EO (70% ai) | 14.5 | 18.125 | 14.5 | 18.125 | 18.125 | 14.5 |
| Cocoamidopropyl betaine (30% ai) | 13.3 | 16.625 | 13.3 | 16.625 | 16.625 | 13.3 |
| Guar hydroxypropyltrimonium chloride | 0.15 | 0.15 | 0.15 | 0.15 | 0.15 | 0.15 |
| Citric acid | 0.325 | 0.325 | 0.35 | 0.325 | 0.325 | 0.325 |
| Sodium benzoate | 0.5 | 0.5 | 0.5 | 0.5 | 0.5 | 0.5 |
| Sodium hydroxide | 0.012 | 0.012 | 0.012 |  |  |  |
| Isopropyl palmitate | 0.5 | 0.5 | 1 | 1.5 | 1 | 0.5 |
| Peach extract | 0.2 | 0.2 | 0.2 | 0.2 | 0.2 | 0.2 |
| PEG-40 hydrog. Castor oil |  |  | 0.5 | 0.5 | 0.5 |  |
| Perfume (Douceur 369) 1.0%, ex. IFF |  |  |  |  | 1 |  |
| Perfume (Caresse 567) 1.0%, ex. IFF |  |  | 1 | 1 |  |  |
| Perfume (Caresse 554) 1.0%, ex. IFF |  |  |  |  |  | 1 |
| Water | q.s. | q.s. | q.s. | q.s. | q.s. | q.s. |
| TOTAL | 95 | 95 | 95 | 95 | 95 | 95 |

Each of the base formulations 4–9, which was to provide 95% by weight of the aqueous base, was modified by the addition of a further sub composition (e.g. in the case of example 4, the addition of components a–h), in the amounts stated. The amounts of the components added in the sub compositions are stated as parts by weight of the aqueous base, with the balance to 100% by weight of the aqueous base being made up by the addition of extra water.

The compositions were then prepared as described above in relation to examples 1–3, dosing the composition with pentane, and assessing its stability, turbidity and consistency after 24 hours. The results are shown below. For dosage purposes, acceptable compositions had to have a base viscosity (prior to pentane dosage) of not more than 9,000 mPa.s, and preferably much less than this.

| | Base-Formulation 4 | | | | | | | |
| --- | --- | --- | --- | --- | --- | --- | --- | --- |
| | a | b | c | d | E | f | g | h |
| Isopropyl palmitate | 0.50 | 0.80 | 0.50 | 0.50 | 0.80 | 1.00 | 1.00 | 0.90 |
| PEG-120 methyl glucose dioleate | 1.80 | 2.50 | 2.00 | 2.00 | 2.00 | 2.50 | 2.00 | 2.50 |
| Propylene Glycol | 0.00 | 0.00 | 0.00 | 0.20 | 0.00 | 0.00 | 0.00 | 0.00 |

-continued

| | Base-Formulation 4 | | | | | | | |
|---|---|---|---|---|---|---|---|---|
| | a | b | c | d | E | f | g | h |
| Base Viscosity/mPas | | | | | | | | |
| Douceur 369 | 4640 | 795 | 5775 | 5400 | | | | |
| Mousseline 945 | 8150 | 1700 | 10000 | 8300 | | | | |
| Caresse 567 | 12700 | 3500 | 14450 | 14900 | 1370 | 853 | 133 | 1710 |
| | sp/tur/co | sp/tur/co | sp/tur/co | sp/tur/co | sp/tur/co | sp/tur/co | sp/tur/co | sp/tur/co |
| Douceur 369 | | | | | | | | |
| Properties of Gel | | | | | | | | |
| + 5% Pentane | −/−/− | +/−/+ | −/−/+ | +/−/+ | | | | |
| + 10% Pentane | −/−−/+ | +/−−/++ | +/−−/+ | −−/−−/+ | | | | |
| Mousseline 945 | | | | | | | | |
| Properties of Gel | −/−/+ | +/−/+ | −−/−−/+ | −−/−/+ | | | | |
| + 5% Pentane | | | | | | | | |
| + 10% Pentane | −/−−/+ | −−/−−/++ | −−/−−/++ | −−/−−/++ | | | | |
| Caresse 567 | | | | | | | | |
| Properties of Gel | | | | | | | | |
| + 5% Pentane | −/−/+ | −/−/+ | −/−/+ | −−/−/+ | −−/−/− | −−/−−/+ | −−/−/− | +/−/+ |
| + 10% Pentane | −/−−/+ | −/−−/++ | −−/−−/++ | −−/−/+ | −−/−−/+ | −−/−−/++ | −−/−/++ | +/−−/++ | sp = separation −− = severe separation − = slight separation + = no separation
tur = turbidity −− = very turbid − = slightly turbid + = clear
co = consistency − = not thickened + = thickened ++ = gelled Suitable compositions after the stability tests described have no separation (ie +), are at least thickened or gelled (ie+ or ++), and may be slightly turbid or clear (ie − or +). The results indicate that suitable compositions according to the criteria applied are compositions 4b (Douceur 369), 4d (Douceur 369a), 4b (Mousseline 945) and 4h (Caresse 567), all with 5% pentane.

The results indicate that suitable compositions according to the invention under the criteria applied are compositions 5p (Douceur 369) and 5o (Mousseline 945) both with 5% pentane, and also 5p (Douceur 369) and 5o (Mousseline 945), both with 10% pentane.

| | Base-Formulation 5 | | | | | |
|---|---|---|---|---|---|---|
| | k | l | m | n | o | p |
| Isopropyl palmitate | 0.80 | 1.00 | 2.00 | 1.00 | 1.50 | 1.4 |
| PEG-120 methyl glucose dioleate | 2.50 | 2.50 | 2.50 | 2.50 | 2.50 | 2.5 |
| Propylene Glycol | 0.00 | 0.00 | 0.00 | 1.00 | 0.00 | 0.00 |
| Base Viscosity/mPas | | | | | | |
| Douceur 369 | 39300 | | 70 | 13550 | | 2740 |
| Mouseline 945 | | 20600 | 81 | 18700 | 1300 | |
| Caresse 567 | | 35000 | 170 | 26400 | 5750 | |
| | sp/tur/co | Sp/tur/co | sp/tur/co | sp/tur/co | sp/tur/co | sp/tur/co |
| Douceur 369 | | | | | | |
| Properties of Gel | | | | | | |
| + 5% Pentane | | | | | | +/−/+ |
| + 10% Pentane | | | | | | +/−/++ |
| Mousseline 945 | | | | | | |
| Properties of Gel | | | | | | |
| + 5% Pentane | | | | | +/−/+ | |
| + 10% Pentane | | | | | +/−/++ | |
| Caresse 567 | | | | | | |
| Properties of Gel | | | | | | |
| + 5% Pentane | | | | | −/−/+ | |
| + 10% Pentane | | | | | −−/−−/++ | |

|  | Base-Formulation 6 | | | Base-Formulation 7 | | | |
| --- | --- | --- | --- | --- | --- | --- | --- |
|  | q | r | s | t | u | v | w |
| Isopropyl palmitate | 1.00 | 1.00 | 1.00 | 2.00 | 2.00 | 1.50 | 1.50 |
| PEG-120 methyl glucose dioleate | 2.80 | 2.40 | 2.00 | 2.80 | 2.50 | 2.00 | 2.20 |
| PEG-40 Hydrogenated castor oil | 0.50 | 0.50 | 0.50 | 0.50 | 0.50 | 0.50 | 0.50 |
| Base Viscosity/ mPas (Haake VT500 Stufe 5) Caresse 567 | 291 | 116 | 70 | 318 | 148 | 674 | 1130 |
| Properties of Gel |  |  |  |  |  |  |  |
| + 5% Pentane | +/−/+ | +/−/+ | +/−/+ | +/−/++ | +/−/+ | +/+/− | +/+/+ |
| + 10% Pentane | +/−/++ | +/−−/++ | +/−−/++ | +/−/++ | +/−/++ | +/−/++ | +/−/++ |

The results indicate that suitable compositions according to the invention under the criteria applied are compositions 6q, 6r, 6s, 7t, 7u and 7w, with Caresse 567 at 5% pentane, and compositions 6q, 7t, 7u, 7v and 7w, all with Carewsse 567 at 10% pentane.

consistency tests described above. The consistency test is significant, as the dispersed composition should be in the form of a gel or thick liquid. The nature of the package in which the composition is typically stored (eg bag in can, or elasticated bladder) suggests that the composition is note

|  | Base-Formulation 8 | | | Base Formulation 9 | | |
| --- | --- | --- | --- | --- | --- | --- |
|  | x | y | z | Fa | Fb | Fc |
| Isopropyl palmitate | 1.50 | 1.50 | 1.50 | 0.50 | 0.70 | 1.00 |
| PEG-120 methyl glucose dioleate | 2.50 | 2.10 | 1.80 | 2.50 | 2.50 | 2.50 |
| PEG-40 hydrogenated castor oil | 0.50 | 0.50 | 0.50 | — | — | — |
| Base Viscosity/ mPas |  |  |  |  |  |  |
| Douceur 369 Mousseline 945 | 963 | 306 | 208 |  |  |  |
| Caresse 945 |  |  |  | 7680 | 1240 | 106 |
|  | Sp/tur/co | sp/tur/co | sp/tur/co | sp/tur/co | sp/tur/co | sp/tur/co |
| Douceur 369 |  |  |  |  |  |  |
| Properties of Gel |  |  |  |  |  |  |
| + 5% Pentane | +/+/− | −/+/− | −/+/+ |  |  |  |
| + 10% Pentane | −/−/+ | +/−/++ | +/−/+ |  |  |  |
| Caresse 554 |  |  |  |  |  |  |
| Properties of Gel |  |  |  |  |  |  |
| + 5% Pentane |  |  |  | +/+/+ | +/+/+ | +/+/+ |
| + 10% Pentane |  |  |  | −/−/+ | −−/−−/+ | +/−/+ |

The results indicate that suitable compositions according to the invention under the criteria applied are compositions 8y and 8z with Douceur 369 at 10% pentane, compositions 9Fa, 9Fb, 9Fc with Caresse 554 at 5% pentane, and composition 9Fc with Caresse 554 at 10% pentane.

As the skilled person will appreciate from the foregoing, compositions according to the invention may be adjusted by routine and minor adjustment of the hydrophobic component of the composition, such as the benefit agent, the self foaming agent and the perfume oil, to reliably produce satisfactory compositions.

It is also highly preferable that compositions according to the invention fulfil all of the separation, turbidity and readily homogenised once packaged, for example by shaking so product separation is undesirable. The turbidity test is indicative of long term stability of the formulation.

EXAMPLES 10–12

The following compositions were prepared as outlined above:

|  | 10 | 11 | 12 |
|---|---|---|---|
| SLES.2EO | 18.2 | 18.2 | 13.2 |
| Cocoamidopropyl betaine | — | — | 5.0 |
| Arlatone T (PEG 40 sorbitan peroleate) | 7.0 | 7.0 | 7.0 |
| PEG-40 Hydrog. castor oil | — | — | — |
| PEG-120 methyl glucose dioleate | — | — | — |
| Isopropyl palmitate (Estol 1517) | — | — | — |
| Isopropyl myristate (Estol 1514) | 3.0 | 3.0 | 3.0 |
| Perfume (Caresse 567, ex. IFF) | 2.0 | 2.0 | 2.0 |
| Guar hydroxypropyltrimonium chloride | — | — | — |
| Citric acid | — | — | — |
| Sodium benzoate | — | — | — |
| Sorbitol | 2.1 | — | 2.1 |
| Water |  | To 100 |  |

The compositions were dosed into bag in can packaging, and assessed for their properties.

In addition, as in examples 4–9 above, the compositions were assessed for nature of the gel they provided, when dosed with both 5% and 10% pentane as a post foaming agent. Classification of the gel is as outlined in conjunction with examples 4–9 above.

Results

| Example | 10 | 11 | 12 |
|---|---|---|---|
| pH | 6.9 | 7.0 | 6.4 |
| Base viscosity (mPas) | 128 | 122 | 251 |

| Example |  | 10 | 11 | 12 |
|---|---|---|---|---|
| Separation/ Turbidity/ Consistency; | 5% pentane | +/+/++ | +/+/++ | −/−−/− |
|  | 10% pentane | +/+/++ | +/+/++ |  |

Examples 10 and 11 coincide with examples 11 and 12 of GB 2213160 referred to above. Example 12 coincides with example 11 of GB 2213160, but with 5.0% cocamidopropyl betaine added. As can be seen, example 12 is unstable, indicating that amphoteric surfactants would not be expected to be usable in compositions according to the teaching of GB 2213160.

What is claimed is:

1. A package or container comprising an aqueous self foaming viscous liquid or gel cleansing composition comprising:
   (a) a base composition comprising a surfactant system comprising an anionic surfactant and an amphoteric or zwitterionic surfactant and a hydrophobic component; and
   (b) a post foaming agent;
   wherein the cleansing composition is substantially free of soap;
   wherein said post foaming agent (b) is dosed into the base composition (a) within one minute of dosing the aqueous cleansing composition into said package or container such that said post foaming agent containing base composition does not thicken to form said viscous liquid or gel until the base composition is inside said package or container and thickens prior to dispensing said self-foaming cleansing compositions.

2. A package or container according to claim 1, wherein the composition additionally comprises a nonionic or a cationic surfactant.

3. A package or container according to claim 1, wherein the base composition has a viscosity prior to mixing with the post foaming agent and being dosed into the package of 9,000 mPa.s or less.

4. A package or container according to claim 3, wherein the viscosity of said cleansing composition is less than 8,000 mPa.s.

5. A package of container according to claim 4, wherein the viscosity is less than 3,000 mPa.s.

6. A package or container according to claim 1, wherein said cleansing composition is in a bag in said package or container.

7. A package or container according to claim 1, wherein the post foaming agent is dosed into the base composition within 10 seconds of said aqueous cleansing composition being dosed into the bag.

8. A package or container according to claim 1, wherein the post foaming agent is dosed into the base composition within 1 second of said aqueous cleansing composition being dosed into the bag.

9. A package or container according to claim 1, wherein said aqueous cleansing composition additionally comprises a propelling gas in sufficient quantities to generate a dispensing pressure, which dispensing pressure is between 3 and 9 bar.

10. A package or container according to claim 1, wherein the package or container is an elasticated bladder container.

11. A package or container according to claim 1, wherein the post foaming agent is present in the composition at levels of 4 to 15% by weight of the composition.

12. A package or container according to claim 1, wherein the composition is in the form of an isotropic blend.

13. A package or container according to claim 1, wherein the composition is in the form of a microemulsion.

14. A package or container according to claim 1, wherein the composition contains less than about 1% by weight of soap.

15. A package or container according to claim 1, wherein the past foaming agent is a volatile or liquifiable hydrocarbon.

16. A package or container according to claim 1, having no headspace.

17. A package or container, according to claim 1, wherein the hydrophobic component comprises isopropyl palmitate or isopropyl myristate.

18. A package or container according to claim 1, wherein the hydrophobic component comprises 0.1–20% by weight of the composition of a hydrophobic benefit agent.

19. A package or container according to claim 1, wherein said aqueous cleansing composition additionally comprises a cationic polymer.

20. A package or container according to claim 1, wherein the composition is not separated after twenty four hours.

21. A package or container according to claim 1, wherein the post foaming agent is n-pentane.

* * * * *